United States Patent [19]

Esper et al.

[11] Patent Number: 4,532,492
[45] Date of Patent: Jul. 30, 1985

[54] TEMPERATURE-COMPENSATED, OXYGEN-CONTENT GAS SENSOR

[75] Inventors: Friedrich J. Esper, Leonberg; Hermann Fischer, Stuttgart; Karl-Hermann Friese; Peter Scharner, both of Leonberg, all of Fed. Rep. of Germany

[73] Assignee: Robert Bosch GmbH, Stuttgart, Fed. Rep. of Germany

[21] Appl. No.: 620,717

[22] Filed: Jun. 14, 1984

[30] Foreign Application Priority Data

Jun. 23, 1983 [DE] Fed. Rep. of Germany ....... 3322534

[51] Int. Cl.³ ............................................. G01N 27/12
[52] U.S. Cl. ......................................... 338/34; 73/23; 73/27 R; 422/98
[58] Field of Search ............... 338/34, 14, 7–9; 73/23, 27 R; 422/94–98

[56] References Cited

U.S. PATENT DOCUMENTS

| 4,147,513 | 4/1979 | Bienkowski et al. ........... 73/23 X |
| 4,208,786 | 6/1980 | Merchant et al. ........... 338/14 X |
| 4,225,842 | 9/1980 | Schlesselman et al. ........... 73/23 X |
| 4,234,542 | 11/1980 | Romine ........... 73/23 X |
| 4,453,397 | 6/1984 | Ohta et al. ........... 338/34 X |

FOREIGN PATENT DOCUMENTS

| 2753035 | 6/1978 | Fed. Rep. of Germany ........ 422/94 |
| 3221627 | 12/1982 | Fed. Rep. of Germany .......... 73/23 |
| 52-37486 | 3/1977 | Japan ................................. 422/98 |

OTHER PUBLICATIONS

Logothetis et al., "TiO₂ Film O₂ Sensors made by CVD from Organomettallics", Sensors & Actuators, vol. 4, 1983, pp. 333–340.

Primary Examiner—Roy N. Envall, Jr.
Assistant Examiner—C. N. Sears
Attorney, Agent, or Firm—Frishauf, Holtz, Goodman & Woodward

[57] ABSTRACT

To simplify manufacture and assembly of a temperature-compensated titanium dioxide oxygen sensor, the sensor (9, 9') is applied as a layer on the thermistor body (1), with an electrode (8) interposed; preferably, the thermistor body is densely sintered titanium dioxide, in the form of a closed tube (1, 1') which may have a central opening (FIG. 1: 2) therethrough, with the sensor body being porous titanium dioxide and located either on the inside (FIG. 1) surface of the thermistor body (1) or on the outside (FIG. 2) surface, and supported by the thermistor body, which forms the substrate and support surface for the sensor body.

9 Claims, 2 Drawing Figures

TEMPERATURE-COMPENSATED, OXYGEN-CONTENT GAS SENSOR

REFERENCE TO RELATED APPLICATION

U.S. Pat. No. 4,151,503, filed Oct. 5, 1977, now U.S. Pat. No. 4,151,503.

The present invention relates to a gas sensor, and more particularly to a sensor which can determine the oxygen content in gases, particularly exhaust gases from an internal combustion engine (ICE) which is temperature-compensated, and which operates on the principle of resistance measurement.

BACKGROUND

Resistance measurement-type sensors are known, see Published European Pat. No. 0 001 510, to which U.S. Pat. No. 4,151,503 filed Oct. 5, 1977, now U.S. Pat. No. 4,151,503, corresponds. The sensor there described has a sensing element made of titanium dioxide, the resistance of which changes with oxygen partial pressure to which the sensor is exposed. The titanium oxide, however, not only changes resistance with respect to oxygen partial pressure but, also, with respect to temperature. The sensor described in the referenced patents, therefore, includes a second sensing element which also may be made of titanium dioxide, and which is so constructed that the resistance hardly changes with change in oxygen partial pressure, but which changes only in relation to temperature. The second sensing element then is used to permit compensation for temperature of the output from the actual oxygen sensing component of the overall sensor.

The sensor as described is comparatively complex, requiring special support tubes to carry the sensing elements, constructed in the form of disks or pills, and connected by means of wires which, at the same time, form supports and electrical conductors. The overall construction of the sensor is difficult to carry out, requiring manufacturing technology which is complex, and resulting in prices for the sensors which are comparatively high.

THE INVENTION

It is an object to provide a sensor which has the advantage of the simplicity of a resistance-type oxygen sensor with an additional temperature compensating element, in short, with a thermistor, which can be easily constructed, does not require special manufacturing technology, and which can be efficiently made by well known manufacturing processes.

Briefly, the sensor and thermistor are so made that the oxygen sensor, which is made of a porous oxygen partial pressure responsive resistance material, is supported on the thermistor body which is made of a densely sintered resistance material. Thus, the thermistor body serves as support and substrate for the oxygen sensor, while being exposed to the same temperature influences, thereby providing efficient temperature compensation. An electrode, typically an electrode layer, made, for example, in thin-film technology, is interposed between the densely sintered resistance material of the thermistor body and the porous resistance material of the sensor body.

In accordance with a preferred embodiment of the invention, both the thermistor body and the sensor body comprise titanium dioxide; the same base material, thus, can be used, the sensor body, during manufacture, having had added thereto a material which will render it porous during sintering, for example a volatile pore-forming material which thus will change the physical structure of the titanium dioxide forming the oxygen sensor from the physical structure of the densely sintered thermistor body.

The structure has the advantage that no specific carrier or support structure will be needed for the sensor itself, since the temperature sensing element, or thermistor, will form the support; thus, a specific substrate for the sensor is no longer necessary, and the manufacturing technology can be simple and correspond to that which is well known in the manufacture of oxygen partial pressure sensors operating on the potentiometric principle, also known as lambda sensors. The arrangement also permits manufacture in one operating step, by making the thermistor and sensor in a single sintering process, and combining thermistor and sensor by this sintering process into a single unit.

In accordance with a preferred embodiment of the invention, the thermistor which forms the carrier for the sensor is made in the shape of a tube closed at one end, which can readily be assembled in a housing body known, for example, in the manufacture of the aforementioned lambda sensors.

DRAWINGS

FIG. 1 is a longitudinal schematic cross-sectional view through a sensor in accordance with the present invention; and FIG. 2 illustrates another embodiment in which the sensor is located at the outside of the thermistor tube.

DETAILED DESCRIPTION

Figure 1:
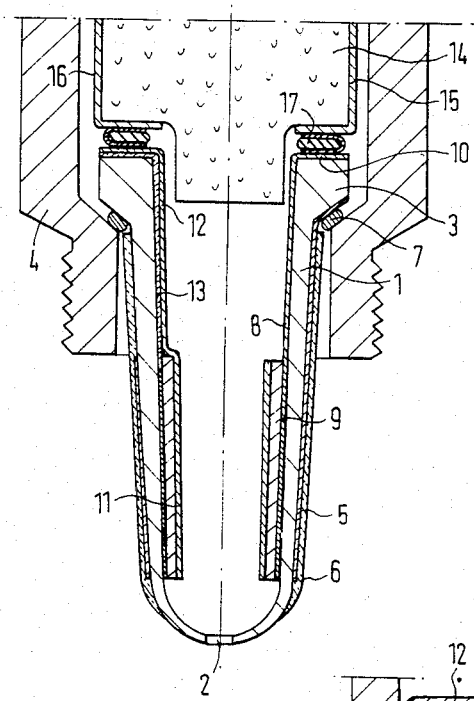

The resistance sensor unit has a closed tube 1 made of densely sintered titanium dioxide. The tube 1 forms the body for the thermistor. The cup or dome-shaped end is formed with an opening 2 therein to permit ingress of gases to the interior of the tube. The rearward, open end of the tube is formed with a shoulder 3 to permit seating of the tube within a housing, for example of the standard and well-known lambda-sensor construction. Housing 4 which may, for example, be of steel, has an interior shoulder against which the shoulder 3 can fit, with the interposition of a metallic sealing ring 7.

The thermistor body 1 has an outer electrode 5 applied thereto, which can be protected by an external protective cover layer 6. The outer electrode 5 is continued, for example in form of a conductive track, to the outer inclined surface of the shoulder 3 where it is electrically connected by the metallic sealing ring 7 with the metallic housing 4. The inner wall of the thermistor body 1 has an inner electrode 8 applied thereto which, simultaneously, forms one electrode for the thermistor and an electrode for the oxygen gas sensing element 9. The oxygen gas sensor 9 likewise is made of titanium dioxide and may be constructed in form of a ring, which can be slightly conical to fit essentially against the inner conical surface of the thermistor body 1. The inner electrode 8 is extended in form of a conductive track 10 to the upper surface of the shoulder 3. The sensor 9 is constructed in form of a porous layer located in the interior of the thermistor body, and has a porous electrode 11 located at the side opposite the thermistor body. The electrode 11 is continued in form of a conductive track 12 to the horizontal upper surface of the shoulder 3. It is not directly applied to the inner wall of the thermistor body 1, but, rather, is separated therefrom by an insulating intermediate layer 13 which, for example, may be a glaze of barium silicate glass.

An insulating ceramic 14 extends into the interior of the thermistor body 1, and is formed with two shoulders, the insulating body 14 having conductive tracks 15, 16, or other electrical conductors applied to respectively opposite or diametrically positioned surfaces thereof. An electrically insulating sealing ring 17 is located between the ceramic body 14 and the horizontal surface of the shoulder 3. The insulating ring 17 has metallic strips surrounding the insulating ring 17 in the region of the two conductive tracks or conductors 10, 12, and the conductors 15, 16 on the body 14, in order to form an electrical connection between the conductive tracks 10-15 and 12-16, respectively. The insulating body 14 is held in compressed position in the housing 4, for example by a rolled-over ring overlapping the insulating body 4, or rolled-over tabs, as well known from lambda-sensor constructions; any other suitable way of holding the body 14 can be used, for example a compression spring abutted against an in-turned shoulder on the body 4.

Manufacture of the sensor is simple: First, the thermistor body 1 is made of compressed titanium dioxide powder, which is pre-sintered, or pre-heated, for example to low incandescence. Electrodes 5 and 8 are then applied, the electrodes being made, for example, of about 40% (by volume) of titanium dioxide, the remainder platinum. Application may be in form of a paste, for example by thick-film technology, which paste is dried. The layer, which will then form the sensor 9, is applied to the inside of the titanium dioxide tube, and, thereafter, the electrode 11 is applied to the exposed surface of the sensor. The insulating layer 13, as well as conductive tracks 10 and 12, are then applied. The composition of the electrode 11, as well as of conductive tracks 10 and 12, may be similar to that of electrodes 5 and 8. The protective layer 6, which may also be made of titanium dioxide, is then applied to the outside of the tube, and the entire composite unit is sintered at a temperature of from between 1300° C. to 1450° C. During the sintering process, the thermistor body 1 will become densely sintered. To insure that, during the sintering process, the thermistor body 1 will be densely sintered whereas the sensor 9 will remain porous, the titanium dioxide powder selected for the thermistor body will include a higher proportion of rutile than customary; the titanium dioxide powder for the sensor 9 will have a pore-forming substance added thereto, for example ammonium carbonate. The conditions of preparation and later on working and sintering of the respective elements, likewise, may be matched to the eventual requirements of a densely sintered body 1 and a porous body 9, as is well known in titanium dioxide and sintering technology.

The sensor element 9 need not be applied as a layer on the inner surface of the tube 1—with the electrode 8 interposed—but may be introduced as a separately manufactured tubular element, for example of slightly tapering form, to fit into the inwardly slightly tapering surface of the tube 1. It may, thus, be made as a pre-manufactured subassembly in form of a ceramic tube, introduced into the tube 1 before the final sintering process. In order to insure a tight seat of the sensor 9, the slightly conical form as shown in FIG. 1 for the inner opening of the thermistor body 1 is desirable. The shape, also, has this advantage: During sintering, the thermistor body 1, which is tightly and densely sintered, will shrink somewhat more than the body 9, which will remain porous due to the addition of the pore-forming substances in manufacture. During sintering, then, the thermistor body 1 will shrink more than the sensor body 9, and will be tightly retained therein. The connection between the sensor body 9 and the thermistor body 1 then is effected by the intermediate electrode 8 during the sintering step.

Figure 2:
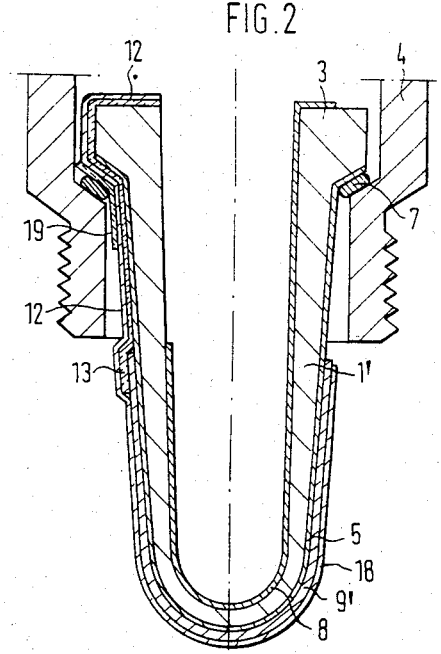

The structure in accordance with FIG. 2 is similar to that of FIG. 1, and the same elements have been given the same reference numerals; the difference is that the thermistor body 1' does not have the central bore 2 leading into the opening, but, rather, has a closed cup-shaped end. The gas sensor 9' is then applied as a layer to the outside of the thermistor body 1'. The outer surface of the sensor 9' has an electrode 18 applied thereto which is carried out in form of a conductive track to the horizontal portion of the shoulder 3 at the left side of FIG. 2. It is necessary to insulate the conductive track by an insulating layer 13, for example a glaze, with respect to the thermistor body. The conductive track 12 must also be insulated in the region of the sealing ring 7 by a further insulating layer 19, for example also in form of a glaze, to electrically insulate the track 12 from the metallic ring 7 and thus the housing 4. The contacting arrangement for the electrodes 8 and 12, not shown in FIG. 2, can be identical to the arrangement described in connection with FIG. 1.

Electrode 18 and sensor 9 can be covered by a porous protective layer—not shown in FIG. 2—for example made of aluminum oxide or the like.

Manufacture of the sensor as shown in FIG. 2 as analogous to that described in connection with the sensor of FIG. 1. It is only necessary to apply the respective glazing layers, and the portions of the conductive tracks thereon which are to be applied, after the sintering processes; glazing layers are melted-on at lower than sintering temperatures, for example between about 1100° C. to 1250° C.

Various changes and modifications may be made, and any features described may be used with any of the others, within the scope of the inventive concept.

We claim:

1. Temperature-compensated oxygen-content gas sensor, to determine the oxygen content in gases, typically exhaust gases from an internal combustion engine (ICE), having
   an oxygen-responsive sensor body (9) comprising a semiconductive metal oxide;
   a thermistor body (1) located in thermally coupled relation to the oxygen-responsive sensor body (9) and comprising a material changing its resistance value with temperature;
   and electrodes coupled to the oxygen-responsive sensor body (9) and to the thermistor body (1),
   wherein, in accordance with the invention, the thermistor body (1) is a tubular structure having a cupped end;
   the material of the thermistor body (1) comprises a densely sintered resistance material and forms a substrate and support for the sensor body (9);
   and wherein the sensor body (9) comprises a porous resistance material and is applied against a surface of the thermistor body (1), with an electrode (8), which is in the form of a layer, interposed between the thermistor body (1) and the sensor body (9).

2. Sensor according to claim 1, wherein said interposed electrode (8) forms a common electrode for both the thermistor body and the sensor body.

3. Sensor according to claim 1, wherein the material of the sensor body (9) and of the thermistor body (1) both comprise titanium dioxide.

4. Sensor according to claim 1, wherein the cupped end of the thermistor body has a through-opening (2);
and the sensor body is located on an inside surface of the tubular thermistor structure, with said electrode interposed therebetween.

5. Sensor according to claim 4, wherein the thermistor body comprises densely sintered material;
and the sensor body comprises porous sintered material secured to the thermistor body by a shrink-fit, with said electrode (8) interposed,
said shrink-fit being generated by shrinkage of the densely sintered thermistor body against the porous sensor body (9) during sintering-together of the thermistor body and the sensor body, with said electrode interposed.

6. Sensor according to claim 1, wherein the sensor body comprises a layer (9') located at the outside of the tubular structure forming the thermistor body (1'), with an electrode layer (5) interposed between the thermistor body (1') and the sensor body (9').

7. Sensor according to claim 4, wherein the material of the sensor body (9) and of the thermistor body (1) both comprise titanium dioxide.

8. Sensor according to claim 5, wherein the material of the sensor body (9) and of the thermistor body (1) both comprise titanium dioxide.

9. Sensor according to claim 6, wherein the material of the sensor body (9) and of the thermistor body (1) both comprise titanium dioxide.

* * * * *